(12) United States Patent
Giedigkeit et al.

(10) Patent No.: US 8,338,654 B2
(45) Date of Patent: Dec. 25, 2012

(54) HYDROGENATION PROCESS USING CATALYST COMPRISING ORDERED INTERMETALLIC COMPOUND

(75) Inventors: Rainer Giedigkeit, Dresden (DE); Marc Armbruester, Dresden (DE); Kirill Kovnir, Tallahassee, FL (US); Juri Grin, Dresden (DE); Robert Schloegl, Berlin (DE); Juergen Osswald, Luebeck (DE); Thorsten Kessler, Stahnsdorf (DE); Rolf E. Jentoft, Norman, OK (US)

(73) Assignee: Max-Planck-Gesellschaft zur Foerderung der Wissenschaften E.V., Munich (DE)

( * ) Notice: Subject to any disclaimer, the term of this patent is extended or adjusted under 35 U.S.C. 154(b) by 859 days.

(21) Appl. No.: 12/282,920

(22) PCT Filed: Mar. 15, 2007

(86) PCT No.: PCT/EP2007/002325
§ 371 (c)(1),
(2), (4) Date: Jan. 5, 2009

(87) PCT Pub. No.: WO2007/104569
PCT Pub. Date: Sep. 20, 2007

(65) Prior Publication Data
US 2009/0221861 A1 Sep. 3, 2009

(30) Foreign Application Priority Data
Mar. 15, 2006 (EP) ..................... 06005310

(51) Int. Cl.
*C07C 5/08* (2006.01)
*B01J 23/62* (2006.01)

(52) U.S. Cl. ........ 585/259; 585/250; 585/258; 585/260; 585/271; 585/275; 585/277; 502/300; 502/325; 502/332; 502/333

(58) Field of Classification Search ................. 585/250, 585/258, 259, 260, 271, 275, 277; 502/300, 502/325, 332, 333
See application file for complete search history.

(56) References Cited

U.S. PATENT DOCUMENTS 4,120,763 A 10/1978 Breda et al.
4,507,401 A * 3/1985 Dubois et al. ................ 502/242

(Continued)

FOREIGN PATENT DOCUMENTS

DE 1137003 9/1962

(Continued)

OTHER PUBLICATIONS

Kovnir, et al., "PdGa and Pd3Ga7: Highly Selective Catalysts for the Acetylene Partial Hydrogenation" in Scientific Bases for the Preparation of Heterogeneous Catalysts, E. M. Gaigneaux, et al., eds., pp. 481-488, Elsevier, 2006 (month unknown).*

(Continued)

*Primary Examiner* — In Suk Bullock
*Assistant Examiner* — Bradley Etherton
(74) *Attorney, Agent, or Firm* — Harness, Dickey & Pierce, PLC

(57) ABSTRACT

Selective hydrogenation of unsaturated hydrocarbon compounds, e.g. of acetylene to ethylene, uses a hydrogenation catalyst comprising an ordered intermetallic compound. The ordered intermetallic compound comprises at least one metal of type A capable of activating hydrogen, and at least one metal of type B not capable of activating hydrogen. The structure of the ordered intermetallic compound is such that the type A metal is mainly surrounded by atoms of the type B metal.

12 Claims, 6 Drawing Sheets

U.S. PATENT DOCUMENTS

| | | | |
|---|---|---|---|
| 5,219,816 A | 6/1993 | Zhou et al. | |
| 5,364,998 A * | 11/1994 | Sarrazin et al. | 585/259 |
| 5,536,694 A * | 7/1996 | Schuetz et al. | 502/301 |
| 5,559,065 A * | 9/1996 | Lauth et al. | 502/5 |
| 5,866,734 A * | 2/1999 | Flick et al. | 585/260 |
| 6,005,145 A * | 12/1999 | Cordier et al. | 564/490 |
| 6,127,310 A * | 10/2000 | Brown et al. | 502/339 |
| 6,228,800 B1 | 5/2001 | Yamaguchi et al. | |
| 6,245,920 B1 * | 6/2001 | Morikawa et al. | 549/295 |
| 2005/0049445 A1 | 3/2005 | Johnson et al. | |

FOREIGN PATENT DOCUMENTS

| | | |
|---|---|---|
| JP | 63-132848 | 4/1988 |
| JP | 01110594 (D6) | 4/1989 |
| JP | 2005-085607 | 3/2005 |
| JP | 2006-026471 (D3) | 2/2006 |
| WO | WO 98/026867 (D1) | 6/1998 |
| WO | WO 2004/012290 (D2) | 2/2004 |

OTHER PUBLICATIONS

"Ga-Pd Phase Diagram" in ASM Handbook, vol. 3, Alloy Phase Diagrams, 2002, ASM International.*

Komatsu, et al., "Cobalt Intermetallic Compounds for Selective Hydrogenation of Acetylene" in Studies in Surface Science and Catalysis, 101, 1095-1104, J. W. Hightower, et. al., eds., Elsevier, 1996, month unknown.*

Co-Ge Phase Diagram in ASM Handbook, vol. 3, Alloy Phase Diagrams, 2002, ASM International—2002, month unknown.*

Komatsu, et al, "Nano-size Particles of Palladium Intermetallic Compounds as Catalysts for Oxidative Acetoxylation" in Applied Catalysis A: General, 251 (2003), 315-326, available on-line in Jun. 2003.*

Pd-Ga Phase Diagram in ASM Handbook, vol. 3, Alloy Phase Diagrams, 2002, ASM International—2002, month unknown.*

Sarkany, et al., "Hydrogenation of 1-Butene and 1,3-Butadiene Mixtures over Pd/ZnO Catalysts", Journal of Catalysis, 141, 2, 566-582, available Jun. 1993.*

T. Komatsu, et al., Nano-Size Particles of Palladium Intermetallic Compounds as Catalysts for Oxidative Acetoxylation, Applied Catalysis A 251, 2003, 315-326.

A. V. Devekki, Acetoxylation of 1,3-Butadiene in the Presence of Binary Platinoid Intermetallics, Russian Journal of Applied Chemistry 67, 1994, 221-224.

A. V. Devekki, Acetoxylation of 1,3-Butadiene in Presence of Binary Platinoid Intermetollics, Zhurnal Prikladnoi Khimii (Sankt-Peterburg) 67, 1994, 244-248.

N. Iwasa; et al., New Catalytic Functions of Pd-Zn, Pd-Ga, Pd-In, Pt-Zn, Pt-Ga and Pt-In Alloys in the Conversion of Methanol, Catalysis Letters 54, 1998, 119-123.

S. Naito, et al., Remarkable Addition Effect of In and Ga in the NO-CO Reaction over Pd/Si02, Chemistry Letters 1998, 1119-1120.

N. Iwasa, et al., Effect of Zn Addition to Supported Pd Catalysts in the Steam Reforming of Methanol, Applied Catalysis A 248, 2003, 153-160.

N. Iwasa, et al., Selective Hydrogenation of Acetonitrile to Ethylamine Using Palladium-Based Alloy Catalysts, Physical Chemistry Chemical Physics 4, 2002, 5414-5420.

N. Iwasa, et al., New Supported Pd and Pt Alloy Catalysts for Steam Reforming and Dehydrogenation of Methanol, Topics in Catalysis 22, 2003, 215-224.

N. Iwasa, et al., Hydrogen Production by Steam Reforming of Methanol, Journal of Chemical Engineering of Japan 37, 2004, 286-293.

Cao et al. "Supported platinum-gallium catalysts for selective hydordechlorination of Cc14", Journal of Molecular catalysis,vol. 242, No. 1-2, pp. 119-128, Dec. 2005.

Tsud et al, "Electronic Properties of Sn/Pd Intermetallic Compounds on PD (110)" ,Surface Science, vol. 595, No. 1-5, pp. 138-150, Dec. 2005.

Coq et al, "Bimetallic Palladium Catalysts: Influence of the Co-metal on the Catalysts Performance", Jounral of Molecular Catalysis, vol. 173, pp. 117-134, 2001.

E.A. Sales et al, "Liquid-Phase Selective Hydrogenation of Hexa-1,5-diene and Hexa-1,3-diene on Palladium Catalysts. Effect of Tin and Silver Addition" Journal of Catalysis, vol. 195, pp. 96-105, 2000.

H. Zhang, et al., Hydrogen Storage for Carbon Nanotubes Synthesized by the Pyrolysis Method Using Lanthanum Nickel Alloy as Catalyst, Journal of Applied Physics 94, 2003, 6417-6422.

A. Onda, et al., Preparation and Catalytic Properties of Intermetallic Compounds, Research Laboratory of Hydrothermal Chemistry 9, 2001, 93-96.

A. Onda, et al., Characterization and Catalytic Properties of Ni-Sn Intermetallic Compounds in Acetylene Hydrogenation, Physical Chemistry Chemical Physics 2, 2000, 2999-3005.

J. Choi, et al., An Excellent Nickel Boride Catalyst, for the cis-Selective Semihydrogenation of Acetylenes, Tetrahedron Letters 37, 1996, 1057-1060.

T. Komatsu. et al., Cobalt Intermetallic Compounds for Selective Hydrogenation of Acetylene, Studies in Surface Science and Catalysis 101, 1996, 1095-1104.

J. M. B. Branco, Contribution a In Valorisation de Composes Intermetalliques Nickel-et Cuivre-Terres Rares en Catalyse d'Hydrogenation, PhD Thesis, L'Universite Paul Sabatier de Toulouse, 1994.

L. M. Kurashvili, et al., Bi-Components M-ZnO and .11-FeO Catalytic Systems in the Hydrogenation Reactions, 7 Vsesoyuznaya Konferentsiya Kataliticheskie Reaktsii v Zhidkoi Faze part 2, 1988, 49-49.

A. Bahia, et al., Pseudo-Binary Intermetallic Catalysts for Hydrocarbon Conversions, Applied Catalysis 25, 1986, 199-206.

W. Palczewska, et al., Study on Lead Additives in Modified Palladium Catalysts, Journal of Molecular Catalysis 25, 1984, 307-316.

W. Palczewska, et al., Lead and Carbon Monoxide as Additives Modifying the Selectivity of Palladium Catalysts in Partial Hydrogenation of Acetylene, Proceedings of the 8th International Congress of Catalysis, Berlin 4. Verlag Chemie, Weinheim, 1984, 173-183.

F. P. Netzer, et al., Adsorption and Catalysis on Rare Earth Surfaces, in Handbook on the Physics and Chemistry of Rare Earths (Eds. K.A. Gschneidner, L. Eyring), Elsevier, Amsterdam, 1982, 217-320.

S. T. Oyama, et al., Catalysis by Carbides, Nitrides, and Group VII Intermetallic Compounds, Catalysis—Specialist Periodical Report vol. 5, The Chemical Society, London, 1982, 333-365.

J. M. Pountney, et al., A Correlation of Catalytic Behavior with Electronic Structure, Lattice Structure and Surface Composition in Powdered Alloys from the Pseudobinary Systems CeRh3-xPdx and ZrRh3-.xPdx, Surface Technology 8, 1979, 145-159.

L. Schlapbach, et al., A New Mechanism for Lengthening the Lifetime of Hydrogenation Catalysts, Material Research Bulletin 14, 1979, 785-790.

J. M. Pountney, et al., A Comparison of the Electronic and Crystal Structure of some CeRh3-xPdx and ZrRh3-xPdx Alloys and the Catalytic Behavior of some CeRh3-xPdx Alloys, in Institute of Physics Conference Series (Ed. W.D. Corner), 1978, 85-91.

E. L. Muetterties, et al., Catalytic Properties of Metal Phosphides. 1. Qualitative Assay of Catalytic Properties, Journal of the American Chemical Society 96, 1974, 3410 3415.

G. C. Bond, Catalysis by Metals, Academic Press, London, New York, 1962.

Adam et al., "Structure—Reactivity Correlations in the Catalytic Coupling of Ethyne over Novel Bimetallic Pd/Sn Catalysts", J. Phys. Chem. B, vol. 101 (15)(1997), pp. 2979-2805.

* cited by examiner

PdGa $Pd_3Ga_7$

HYDROGENATION PROCESS USING CATALYST COMPRISING ORDERED INTERMETALLIC COMPOUND

FIELD

The present disclosure relates to a process for the hydrogenation, in particular the selective hydrogenation of unsaturated hydrocarbon compounds using a hydrogenation catalyst comprising a specific ordered intermetallic compound, to a catalyst comprising a support and the above specific ordered intermetallic compound supported thereon, and to the use of a binary Pd—Ga ordered intermetallic compound as a catalyst.

BACKGROUND

Selective hydrogenations of unsaturated hydrocarbon compounds are of high industrial significance. The pyrolysis of naphtha for the production of ethene, propene, butanes, 1,3-butadiene and aromatics is a key process in the modern petrochemical industry. For the nearly complete removal of alkynic compounds from the $C_2$, $C_3$ and $C_4$ cuts, selective hydrogenations are generally used.

For instance, the hydrogenation of acetylene is an important industrial process to remove traces of acetylene in the ethylene feed for the production of polyethylene. Because acetylene poisons the catalyst for the polymerisation of ethylene to polyethylene, the acetylene content in the ethylene feed has to be reduced to the low ppm range. Moreover, economic efficiency requires high selectivity of acetylene hydrogenation in the presence of an excess of ethylene to prevent the hydrogenation of ethylene to ethane.

Typical hydrogenation catalysts contain palladium dispersed on metal oxides. While palladium metal exhibits high activity, e.g., in the hydrogenation of acetylene, it possesses only limited selectivity because of the formation of ethane by total hydrogenation and $C_4$ and higher hydrocarbons by oligomerisation reactions.

Modification of palladium catalysts by adding promoters or alloying with other metals has been shown to result in an increased selectivity and long-term stability in acetylene hydrogenation. For instance, increased selectivity in semihydrogenation of alkynes was reported for Pd combined with Ag (U.S. Pat. No. 4,404,124; and D. C. Huang et al., Catal. Lett. 53, 155-159 (1998)), Sn (S. Verdier et al., J. Catal., 218, 288-295 (2003)), Au (T. V. Choudhary et al., Catal. Lett., 86, 1-8 (2003)), Ni (P. Miegge et al., J. Catal., 149, 404-413 (1994), and Pb (W. Palczewska et al., J. Mol. Catal., 25, 307-316 (1984). However, the catalytic performance of these modified Pd catalysts remains insufficient and further improvements in selectivity may decrease the costs for the production of polyethylene. In addition to selectivity, the long-term stability of palladium catalysts has to be improved further.

The $C_3$ cut (propylene) is generally purified by selective hydrogenation of propyne (methylacetylene) and propadiene (allene), and the obtained propylene may be further processed to polypropylene.

Another important selective hydrogenation in industry is the removal of traces of 1,3-butadiene from the $C_4$ fraction after the extractive separation thereof. $Pd/Al_2O_3$ catalysts are commonly used in this reaction. Furthermore, the selective hydrogenation of 1,5-cyclooctadiene, obtained by cyclic dimerization of 1,3-butadiene, to cyclooctene on $Pd/Al_2O_3$ and of benzene to cyclohexene on ruthenium catalysts are of importance.

In all of these selective hydrogenations, further improvements of the selectivity to the desired product and an increased long term stability of the used catalyst have been strongly desired.

The intermetallic compounds PdGa or $Pd_3Ga_7$ are described by E. Hellner et al. in Z. Naturforsch. 2a, 177-183 (1947) and by K. Khalaff et al. in J. Less-Common Met. 37, 129-140 (1974). However, any catalytic potential of these compounds has been unknown so far.

The use of ordered intermetallic compounds as catalysts in a variety of different reactions is generally described in US 2004/0126267 A1 and WO 2004/012290 A2. However, these documents fail to disclose the application of this type of compounds to hydrogenations, let alone selective hydrogenations. In fact, the focus of these references is on their use in fuel cells. In addition, these patent applications fail to disclose the specific Pd based intermetallic compounds of the present invention.

It is therefore an object of the present invention to provide a process for the hydrogenation of unsaturated hydrocarbon compounds, in particular of ethyne (acetylene) in admixture with a large excess of ethene (ethylene) to afford ethene, which overcomes the drawbacks of the prior art as outlined above, and which shows an improved selectivity to the target product. It is another object to provide novel catalysts having the above beneficial properties in selective hydrogenation reactions, in particular in the selective hydrogenation of acetylene to afford ethylene when ethylene is present in an excessive amount.

SUMMARY

The above objects are attained by a process for the hydrogenation of at least one unsaturated hydrocarbon compound using a hydrogenation catalyst comprising a specific ordered intermetallic compound. The ordered intermetallic compound used in the process of the invention comprises at least one metal of type A capable of activating hydrogen, and at least one metal of type B not capable of activating hydrogen, and the structure of the intermetallic compound is such that at least one kind of type A metals is mainly surrounded by atoms of the metal of type B. According to another aspect, the present invention is concerned with a catalyst comprising a support and the above ordered intermetallic compound supported thereon.

According to still another aspect, the present invention relates to the use of a binary Pd—Ga ordered intermetallic compound as a catalyst.

Preferred embodiments of the present invention are subject of the dependent claims.

DRAWINGS

DETAILED DESCRIPTION

Figure 1A:
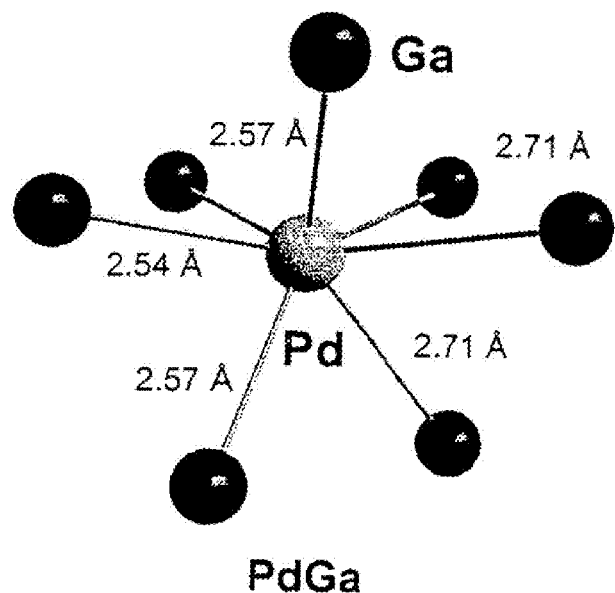
FIG. 1 shows the coordination of Pd atoms in PdGa (FIG. 1a) and in $Pd_3Ga_7$ (FIG. 1b).

The benefits of the hydrogenation process of the present invention can be achieved preferentially if the hydrogenation proceeds selectively.

Everyone active in the field of hydrogenation catalysis is familiar with the term "selective hydrogenations". Generally, a chemical reaction is referred to as being selective if this reacts preferentially with one of several functional groups of similar reactivity which are present in the molecules of the reaction mixture, whereas the remaining functional groups of this type react to a significantly lower degree, i.e. they do hardly react in the case of highly selective reactions. Differently stated, a hydrogenation is selective if this is selecting a certain hydrogenation reaction (or certain hydrogenation reactions) from the various hydrogenation reactions which are possible in the reaction mixture. Consequently, term "selective hydrogenation" as it is used herein covers e.g., the following situations: (1) some of the unsaturations (e.g. double and/or triple bonds) of the unsaturated hydrocarbon compound to be reacted are hydrogenated with preference whereas the other unsaturations react to a significantly lower degree, and (2) in the case that one or more unsaturations of the unsaturated hydrocarbon compound to be reacted can be hydrogenated twice (e.g. triple bonds), they are hydrogenated with preference only once, and the $2^{nd}$ reaction step is hardly observed. For the purpose of the present invention, a hydrogenation is referred to as selective if the molar ratio of the desired target compound to the undesired target compound(s) is larger than 1:1, preferably more than 2:1, more preferably more than 5:1, and most preferably 10:1.

A typical example of situation (1) is the hydrogenation of an alkadiene to afford mainly, preferably almost exclusively, the corresponding alkene without substantial reaction of the alkene to the corresponding alkane. Situation (2) may be exemplified by the reaction of an alkyne to give mainly the corresponding alkene, whereas the consecutive reaction of the alkene to afford the alkane hardly takes place. As will be appreciated from the above, the two situations are not mutually exclusive. That means, both of the above situations may exist in the selective hydrogenation of a specific molecule. In the case of the acetylene reaction in a large excess of ethylene which corresponds to situation (2), it is important that the ethylene, in spite of its large concentration, is hardly converted to ethane.

Examples of selective hydrogenations are described in the Background Art section of the present specification.

The unsaturated hydrocarbon compound used in the selective hydrogenation process of the present invention is not limited in kind as long as this contains one or more unsaturations susceptible to hydrogenation and poses a selectivity problem as outlined above. For example, the unsaturated hydrocarbon compound may be an unsaturated carbonyl compound, e.g. a compound having both a carbonyl moiety and a carbon-carbon double bond in the molecule. However, the unsaturated hydrocarbon compound preferably contains, as unsaturations susceptible to hydrogenation, carbon-carbon double and/or carbon-carbon triple bonds, and is free from further unsaturations susceptible to hydrogenation, i.e. hydrogenable group(s). According to a more preferred embodiment, the unsaturated hydrocarbon compound is selected from the group consisting of alkadienes, alkatrienes and alkapolyenes; alkynes, dialkynes, trialkynes and polyalkynes; and aromatic compounds. The alkadienes, alkatrienes and alkapolyenes, and the alkynes, dialkynes, trialkynes and polyalkynes cover both, alicyclic and cyclic compounds. Still more preferably, the unsaturated hydrocarbon compound is selected from the group of alkadienes, cycloalkadienes, alkynes and benzene.

The alkadiene may be 1,3-butadiene, which will be converted by way of the selective hydrogenation of the present invention, mainly to 1-butene, without being fully hydrogenated to butane to a significant degree. The cycloalkadiene is, for example, 1,5-cyclooctadiene which will afford upon the selective hydrogenation of the invention cyclooctene, while cyclooctane resulting from the full hydrogenation is a minor product. The selective hydrogenation of benzene will afford cyclohexene with minor amounts of cyclohexadiene and cyclohexane. An example of a selective hydrogenation of a triple bond in the presence of a double bond is the purification of 1,3-butadiene by hydrogenation of vinyl acetylene present in the mixture. Still another example of a selective hydrogenation is the reaction of nitrobenzene to aniline.

The alkyne is preferable ethyne (acetylene), and this is the most preferred embodiment of the present invention. Through the process for the selective hydrogenation of the invention, ethyne will predominantly be converted to ethene (ethylene) while the hydrogenation of ethene to afford ethane is negligible. This is even so when the selective hydrogenation of ethyne is carried out under reaction conditions where ethyne is present in admixture with an excess of ethene in relation to ethyne, which is a particularly preferred embodiment of the selective ethyne hydrogenation according to the present invention. Most preferably, ethene is present in the reaction mixture to be hydrogenated in a large excess in relation to ethyne. The ethyne to ethene weight ratio in the starting mixture of the selective ethyne hydrogenation of the invention is preferably 1:10 to $1:10^6$, more preferably 1:50 to $1:10^3$. In industrial processes, the ethene to ethyne weight ratio in the mixture obtained after the selective hydrogenation is typically as large as $>10^6$.

The selective hydrogenation of phenyl acetylene to styrene in excess of styrene is another example of a selective hydrogenation. As will be appreciated, that reaction is the polystyrene counterpart of the selective acetylene hydrogenation in excess of ethylene in the feed used for the preparation of polyethylene.

As used herein, the term "ordered intermetallic compound" refers to a compound that consists of more than one metal and has an ordered crystal structure. For the purpose of the present specification, boron (B), silicon (Si) and arsenic (As) are regarded as "metals" since they can form intermetallic compounds. In the ordered crystal structure, substantially all unit cells include the same arrangement of metal atoms.

The catalyst for use in the invention may be an unsupported or a supported catalyst. If it is an unsupported catalyst, the ordered intermetallic compound may make up at least 90%, preferably at least 95%, more preferably at least 99% of the catalyst. The balance to 100% may, for example, consist of volumes of a non-ordered intermetallic compound which may e.g., be due to the preparation method of the ordered intermetallic compound. Most preferably, the catalyst for use in the selective hydrogenation process of the invention consists entirely of an ordered intermetallic compound.

It will be appreciated that defects which usually cannot be completely avoided in a real crystal may be present in the ordered intermetallic compound. Such defects can cause a small number of unit cells in the ordered intermetallic compound to have a different arrangement of metal atoms than the majority of the unit cells. Defect types include for example vacancies, interstitials, atom substitutions and anti-site defects.

Crystal imperfections due to the presence of defects will lead to a certain homogeneity range of the ordered intermetallic compounds. However, the formulae used in the present specification refer to the ideal crystal structure. As will be appreciated from the above, the stoichiometric ratio of the metals forming the ordered intermetallic compound as used in the formula may vary up and down. To give an example, if a binary ordered intermetallic compound is represented by the general formula $A_xB_y$, then x and y may independently be an integer of 1 or more. In the present specification, AB (i.e. x=y=1) and $A_3B_7$ represent ordered intermetallic compounds having a certain stoichiometric ratio of the constituent metals (for example, PdGa and $Pd_3Ga_7$). Taking account of the above homogeneity range the values of x and y may be slightly greater or slightly less than the whole numbers indicated in the formula. For instance, in the case of AB (i.e. x=y=1), such as in PdGa, the actual values of x or y may be between about 0.9 and 1.1.

The ordered intermetallic compounds of the invention may have a variety of stoichiometric ratios. Preferably, the ordered intermetallic compounds are binary compounds, i.e. those comprising two types of metals, but they may also be ternary or multinary intermetallic compounds. An example of a ternary ordered intermetallic compound for use in the present invention is $Pd_2PtGa_3$.

The ordered intermetallic compounds within the meaning of the present invention are to be distinguished from metal alloys and metal solid solutions. Alloys and solid solutions do not have an ordered atomic structure, as described above. Metal atoms are arranged randomly in unit cells of alloys and solid solutions.

Ordered intermetallic compounds also generally have a more stable atomic arrangement in comparison to alloys and solid solutions. This results in an enhanced lifetime of the catalyst under reaction conditions. In alloys and solid solutions, atoms are prone to migration with an associated reduction of catalytic performance.

Figure 1B:
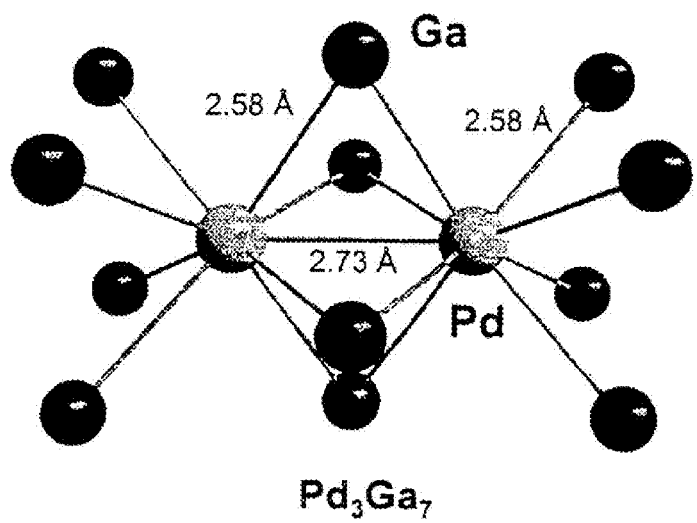

The ordered intermetallic compound for use in the process according to the present invention comprises at least one metal of type A capable of activating hydrogen, and at least one metal of type B not capable of activating hydrogen, and the structure of the ordered intermetallic compound is such that at least one kind of type A metals, preferably all type A metals, is mainly surrounded by atoms of the metal of type B. In this context, the term "mainly" accounts for the fact that there may be defects due to atom substitutions so that there may be some metals of type A in the crystal structure of the intermetallic compound, in the first coordination sphere of which there are also one or more of type A metal atoms. The above requirement of being mainly surrounded is fulfilled if at least 50%, preferably at least 80%, more preferably at least 90%, and most preferably about 100% of the first coordination sphere of least one kind of the type A metals is occupied by atoms of type B metals. The above situation that the type A metal atoms (Pd) are mainly, more specifically exclusively surrounded by type B metal atoms Ga) is illustrated for PdGa in FIG. 1a, and for $Pd_3Ga_7$ in FIG. 1b. The embodiment of the ordered intermetallic compounds for use in the process of the invention where the type A metal atoms are completely surrounded by type B metal atoms, i.e. where about 100% of the first coordination sphere of the at least one kind of type A metal is occupied by atoms of type B metals does, however, not exclude the presence of defects. The feature that the structure of the ordered intermetallic compound is such that at least one kind of type A metals, preferably all type A metals, is surrounded mainly by atoms of the metal of type B indicates that the atoms of type A metal are predominantly coordinated to atoms of type B metals, i.e. coordinated at least 50%, preferably at least 80%, and more preferably about 100% to type B metals.

The molar ratio of the metals of type A and B (A:B) may be from 20:1 to 1:20. Typically it is from 2:1 to 1:20, preferably from 1:1 to 1:20, more preferably from 1:1 to 1:5. The metal of type A is not limited in kind, as long as this is capable of activating hydrogen. However, Cr, Mo, W, Mn, Re, Fe, Ru, Os, Co, Rh, Ir, Ni, Pd, Pt, Cu, Ag, and Au are preferred. Cr, Mo, W, Fe, Co, Rh, Ni, Pd and Pt are more preferred. There is no particular limitation of the metals of type B, either. According to a preferred embodiment, these metals are selected from the group consisting of B, Al, Ga, In, Tl, Si, Ge, Sn, Pb, As, Sb, Bi, Zn, Cd and Hg, i.e. the metals of the groups 12, 13, 14 and 15 of the Periodic Chart. According to a preferred embodiment, the mentioned metals e.g. of the groups 12, 13, 14 and 15 of the Periodic Chart as type B metals are combined with palladium and/or platinum and/or another type A metal to form the ordered intermetallic compound, which is more preferably a binary ordered intermetallic compound.

The intermetallic compound for use in the process of the present invention is more preferably selected from intermetallic compounds of Pd with at least one of B, Al, Ga, In, Tl, Si, Ge, Sn and Zn, intermetallic compounds of Pt with at least one of Al, Ga, In, Tl, Sn and Zn, and intermetallic Pd/Pt compounds with at least one of Al, Ga, In, Tl and Sn, such as $Pd_2PtGa_3$. Preferably, the ordered intermetallic compound is a binary compound of Pd in combination with B, Al, Si, Ge, Zn or Ga, more preferably it is a binary compound of Pd in combination with Ge, Zn or Ga. According to a still more preferred embodiment, the ordered intermetallic compound for use in the process of the present invention is an ordered binary Pd—Ga intermetallic compound. According to another preferred embodiment, the ordered intermetallic compound is a binary compound of Pt in combination with Zn. The above intermetallic compounds, in particular ordered binary intermetallic compounds comprising Pd are preferably used in the selective hydrogenation of carbon-carbon multiple bonds, especially the selective hydrogenation of carbon-carbon triple bonds to give the corresponding alkene. The compounds to be hydrogenated are preferably free of any unsaturated groups amenable to hydrogenation other than the carbon-carbon triple bond(s).

The specific ordered intermetallic compound to be used in the selective hydrogenation process of the present invention is preferably $Pd_2Ga$, PdGa, $PdGa_5$, $Pd_3Ga_7$, PdSn, $PdSn_2$, $Pd_2Ge$, PdZn, PtGa or PtZn; more preferably PdGa, $Pd_2Ga$, $PdGa_5$ or $Pd_3Ga_7$; and most preferably PdGa, $Pd_2Ga$ or $Pd_3Ga_7$. These specific intermetallic compounds may be used in the selective hydrogenation of any unsaturated hydrocarbon, in particular, in the following reactions: (cyclo)alkadiene→(cyclo)alkene and alkyne→alkene (in particular, ethyne→ethene).

In a particular preferred embodiment of the selective hydrogenation process of the invention, the at least one unsaturated hydrocarbon compound is ethyne (acetylene), and the intermetallic compound is an ordered binary Pd—Ga intermetallic compound, preferably PdGa or $Pd_3Ga_7$. Even more preferably, the selective hydrogenation of ethyne to ethene is carried out with the above ordered intermetallic compounds under reaction conditions where the ethyne starting material is present in admixture with ethene, the ethene being present in large excess in relation to ethyne.

It was surprisingly found by the present inventors that intermetallic compounds wherein the intermetallic compound comprises at least one metal of type A capable of activating hydrogen, and at least one metal of type B not capable of activating hydrogen and the structure of the intermetallic compound is such that at least one kind of type A metals is mainly surrounded by atoms of the metal of type B offer distinct advantages in selective hydrogenations, e.g., over the supported monometallic catalysts of the prior art, such as supported palladium, platinum and rhodium catalysts, and over alloyed or promoted palladium catalysts, in terms of selectivity to the desired product. Without wishing to be bound by theory, it is assumed that the enhanced selectivity is due to the defined structure of active sites allowing only certain adsorption geometries of the unsaturated hydrocarbon compound to be hydrogenated. Because the atoms of at least one metal of type A, preferably all type A atoms in the structure of the ordered intermetallic compound are mainly surrounded by type B atoms, the individual atoms of the type A metals are isolated. This is considered to avoid an oversupply of activated hydrogen, and leads to an enhanced selectivity. Due to the isolation of type A atoms, only some adsorption geometries of the reactants are possible.

According to another aspect, the invention is concerned with supported catalysts comprising the ordered intermetallic compounds as described above in connection with the hydrogenation process of the present invention.

Catalyst screening methods may be used to readily determine which ordered intermetallic compounds are well-suited to catalyse a specific type of (selective) hydrogenation. Suitable screening methods are described in A. Hagemeyer, A. Strasser, P. Volpe, F. Anthony, High-throughput screening in heterogeneous catalysis: Technologies, strategies and applications, Wiley-VCh, Weinheim, 2004.

The skilled person in the field of hydrogenation catalysis will readily select and optimise the reaction parameters for a certain selective hydrogenation reaction. For instance, the temperature range of industrial selective hydrogenations is typically 10° to 300° C., preferably 20° to 250° C., most preferably 30° to 200° C. The pressure is generally 1 to 100 bar, preferably 2 to 75 bar, most preferably 5 to 50 bar. For more details, reference is made to WO 03/106020.

The present inventors have found that binary ordered intermetallic compounds comprising palladium and gallium are especially useful selective hydrogenation catalysts, in particular in the selective hydrogenation of acetylene to ethylene. Accordingly, the present invention is directed in another aspect to the use of a binary Pd—Ga ordered intermetallic compound as a catalyst. The present inventors have found that this type of ordered intermetallic compounds offers particular advantages in catalysis, in particular, in the field of selective hydrogenations. Due to their ratio of electronegativities (Pd: 1.4; Ga: 1.8), the palladium is retained in the metallic state but at the same time, a covalent Pd—Ga bond of sufficient strength can be formed. It is considered that these electronic factors lead to the high structural stability of binary Pd—Ga ordered intermetallic compounds. In addition, the covalent bonds are likely to suppress or prevent hydride formation. This avoids an oversupply of active hydrogen which may reduce the selectivity.

For the above reasons, binary Pd—Ga ordered intermetallic compounds were found to be excellent hydrogenation catalysts (in particular, in selective hydrogenation reactions) due to their excellent selectivity and stability. Of course, due to their outstanding stability, they are also promising candidates as catalysts for further types of reactions.

The stoichiometric ratio of Pd and Ga in the ordered intermetallic compound of the invention may be in the range of 20:1 to 1:20. The Pd:Ga range is preferably from 2:1 to 1:20, more preferably from 1:1 to 1:5. Examples of the binary Pd—Ga ordered intermetallic compounds are PdGa, PdGa$_5$, Pd$_3$Ga$_7$, and Pd$_2$Ga. PdGa, Pd$_2$Ga and Pd$_3$Ga$_7$ are particularly preferred. These binary Pd ordered intermetallic compounds, and also Pd$_2$Ge and PdZn have been found to be highly selective hydrogenation catalysts, e.g. in the selective hydrogenation of acetylene to ethylene, even when the acetylene in the feed is admixed with a large excess of ethylene. In addition, PdGa and Pd$_3$Ga$_7$ proved to have an excellent structural stability under various reaction conditions, e.g. in reactive gas atmospheres of hydrogen, various hydrocarbons, carbon monoxide and oxygen, in particular under reaction conditions which are typically employed in industrial selective hydrogenations, e.g. temperatures from room temperature to about 500 K. This renders PdGa and Pd$_3$Ga$_7$ (e.g. in unsupported state) highly attractive catalysts in general, particularly for selective hydrogenations, and especially for the industrial hydrogenation of acetylene in admixture with a large excess of ethylene to afford ethylene with high selectivity.

The ordered intermetallic compounds for use in the process of the invention can for instance be manufactured by melting an amount of the constituent metals suitable to form the intermetallic compound. The metals subjected to the thermal treatment are present in a molar ratio corresponding to their molar ratio in the intermetallic compound. Preferably, the melting of the metals is carried out under inert gas atmosphere, such as argon and nitrogen, preferably argon. This manufacturing method is standard in solid state chemistry. The method of preparing PdGa and Pd$_3$Ga$_7$ is, for example, described in the working examples of the present application, and in more detail in R. Giedigkeit, Diploma thesis, Technische Universität Darmstadt (Germany), 1998, the contents of which is herewith incorporated by reference in its entirety.

The preparation of some ordered intermetallic compounds may involve annealing steps, e.g., where the respective compound does not crystallize from the melt. To give an example, this is necessary for Pd$_3$Ga$_7$ which does not show congruent melting behavior. Looking at the phase diagram of the respective intermetallic system, the skilled person will conclude where annealing is necessary to achieve the thermodynamic equilibrium of the sample so that the thermodynamically most stable modification is formed. The annealing is preferably carried out for an amount of time and temperature as large as possible.

As mentioned earlier, the ordered intermetallic compound for use in the process of the invention may be used in the as-synthesized form as an unsupported catalyst. In this case, the specific surface area (BET method, N$_2$ adsorption, for more details see the Examples) is typically in the range of 0.001 to 0.1 m$^2$/g. To increase the catalyst surface area, so as to enhance the activity of the catalyst, it proved beneficial to comminute (e.g. pulverize) the ordered intermetallic compound. For example, the ordered intermetallic compound obtained by melting the constituent metals as explained above may be comminuted with an associated increased catalyst activity. The means to be used for comminuting (e.g. pulverizing) the ordered intermetallic compound are not limited in kind, and may be ball mills, swing mills, cryo mills, planetary mills, etc. optionally in an argon atmosphere. In the alternative, the ordered intermetallic compounds may be ground by hand, e.g. using a mortar. The above comminution treatments result in a specific surface area of the ordered intermetallic compound which is typically in the range of 0.05 to 20 $m^2/g$, preferably 0.1 to 10 $m^2/g$, and most preferably of 0.2 to 5 $m^2/g$.

To increase the catalytic activity of the ordered intermetallic compounds of the invention, their surface may be subjected to surface etching before they are used as a hydrogenation catalyst in the selective hydrogenation. The surface etching may be carried out prior to or after the comminution treatment; it is preferred to do the etching subsequent to the comminution treatment. However, the ordered intermetallic compounds, e.g., the binary Pd—Ga compounds, are preferably used as catalysts in the unetched state.

The surface etching may be achieved by chemical etching, e.g. by using alkaline etching solutions and complexing amines, such as EDTA and derivatives, dependent on the particular ordered intermetallic compound to be etched. Useful alkaline etching solutions are, for example, aqueous alkali hydroxide (e.g. sodium and potassium hydroxide) and alkaline earth hydroxide solutions, and aqueous ammonia solutions. In the case of ordered intermetallic palladium gallium compounds, in particular of PdGa and $Pd_3Ga_7$, the use of an alkaline etching solution having a pH in the range of 8.0 to 10.5 afforded hydrogenation catalysts showing in the selective hydrogenation of acetylene a higher activity while maintaining an excellent selectivity and catalyst lifetime. In the case of PdGa a pH of about 9.0 and in the case of $Pd_3Ga_7$ a pH of 10.5 gave the best results in terms of activity in the selective hydrogenation of acetylene.

While the catalytic activity of the ordered intermetallic compounds can be increased by way of the surface etching, the selectivity, e.g., in the acetylene reaction, may be slightly reduced upon etching. To regain the selectivity of the unetched ordered intermetallic compound, a tempering at reduced temperature to effect a sintering of the palladium particles can be carried out. Suitable temperatures for the tempering are 50-500° C., preferably 80-400° C., most preferably 100-300° C.

The surface area of the hydrogenation catalyst for use in the process of the present invention may also be increased by using precipitation methods, sol-gel chemistry and inert supports.

According to another aspect, the present invention is concerned with the use of PdGa and $Pd_3Ga_7$ as a catalyst, and to a supported catalyst comprising any of the ordered intermetallic compounds wherein the intermetallic compound comprises at least one metal of type A capable of activating hydrogen, and at least one metal of type B not capable of activating hydrogen and the structure of the intermetallic compound is such that at least one kind of type A metals is mainly surrounded by atoms of the metal of type B, or a mixture of these, provided on a support. Preferred embodiments of the ordered intermetallic compounds in the supported catalysts are the same as those described herein in connection with the hydrogenation process. Suitable supports are those commonly used in catalysis, e.g. compounds having a high surface area, such as active carbon, alumina, silica, silicates, etc.

The following Examples are given for illustration of the invention and must not be construed as limiting the present invention.

EXAMPLES

Preparation of Catalysts

Binary palladium gallium intermetallic compounds were prepared by melting the corresponding amounts of Pd and Ga in glassy carbon crucibles under argon atmosphere in a high-frequency induction furnace. 1.2083 g palladium (ChemPur 99.95%) and 0.7917 g gallium (ChemPur 99.99%) were used to obtain 2 g PdGa (11.354 mmol). 0.7909 g Pd (7.432 mmol) and 1.2091 g Ga (17.340 mmol) yielded 2 g $Pd_3Ga_7$. $Pd_2Ga$ was prepared in a similar way. The crystal structure of the obtained products was controlled by X-ray diffractometry using a STOE STADI P diffractometer (Cu $K_{\alpha1}$ radiation, curved Ge monochromator) in transmission geometry with a linear position sensitive detector and comparison with reference data from literature.

After melting, $Pd_3Ga_7$ was annealed at 673 K for 800 h in a glassy carbon crucible sealed in a silica tube filled with argon. $Pd_2Ga$ was annealed at 1073 K for 170 h in evacuated and sealed quartz ampoules. PdGa was used without further annealing.

The samples were powdered in a swing mill (Retsch MM 200, 4 ml WC pot, 2 WC balls) for 2×30 min for PdGa and 2×10 min for $Pd_3Ga_7$ at 25 Hz. $Pd_2Ga$ was either used as prepared after grinding in a mortar or after milling in Ar atmosphere using the above swing mill for 2×30 min.

$Pd_2Ge$ was prepared by melting the corresponding amounts of Pd and Ge metals in glassy carbon crucibles under argon atmosphere in a high-frequency induction furnace. After the melting the ingot of intermetallic compound was annealed at 1073 K for 170 h in a sealed and evacuated quartz glass ampoule.

PdZn and PtZn were prepared by annealing of the corresponding amounts of metals in evacuated quartz glass ampoules. First ampoules were heated up to 873 K for 24 h and annealed at this temperature for additional 24 h. Then ampoules were heated up to 1173 K for 24 h and annealed at this temperature for 72 h. According to XRD, PtZn appeared to be a single phase after such temperature treatment, while PdZn was not.

Therefore, PdZn was ground, pressed in a pill and additionally annealed at 1173 K for 3 days. After second annealing single phase material was obtained.

In order to increase the active catalyst surface, chemical etching was performed by ammonia solution at various pH. Commercial ammonia solution (Merck, 25% p.a.) was diluted with water to the required pH value. PH-measurements were performed with a Knick pH-Meter 761 Calimatic and a Mettler-Toledo Inlab 422 electrode calibrated with buffer solutions (Merck centiPUR pH=7 and pH=9). 50 mg PdGa or $Pd_3Ga_7$ were added to 75 ml of the diluted ammonia solution and stirred for 10 minutes at 300 K. The solution was filtrated under Argon flow and washed with additional 50 ml of the diluted ammonia solution. The etched sample was dried by evacuation for 120 min in a desiccator and stored under Ar in a glove box.

Characterization of Catalysts

In the present specification the specific surface area of the intermetallic compounds was measured according to the BET method (Quantachrome Quantasorb Jr.). The samples (200 mg) were treated over night at 393 K in helium flow (20 ml/min) and measurements were performed by determining the total amount of nitrogen adsorbed using three different nitrogen concentrations.

In situ X-ray diffraction (XRD) experiments were conducted on a STOE diffractometer (Cu—$K_\alpha$) in Bragg Brentano geometry equipped with a secondary monochromator, a scintillation counter, and a Bühler HDK high temperature diffraction chamber mounted onto the goniometer. The gases were mixed by Bronkhorst mass flow controller and introduced in the experimental chamber at a total flow of 100 ml/min. The exhaust gas composition was continuously monitored with a mass spectrometer (QMS 200, Pfeiffer). For the in situ experiments usually 50 mg of the samples was dispersed onto a steel band.

The thermal stability of PdGa and $Pd_3Ga_7$ was studied in helium, 20% oxygen in He, or 50% $H_2$ in helium. The in situ XRD patterns for PdGa and $Pd_3Ga_7$ were measured in the 2θ range from 35.5° to 48.5° and from 22.5° to 52.5°, respectively, with a step width of 0.02 and a counting time of 3 sec/step. PdGa and $Pd_3Ga_7$ were heated from 323 K to 723 K and from 323 K to 693 K, respectively, and XRD patterns were measured isothermally every 50 K. The effective heating rate amounted to 0.5 K/min.

Figure 2:
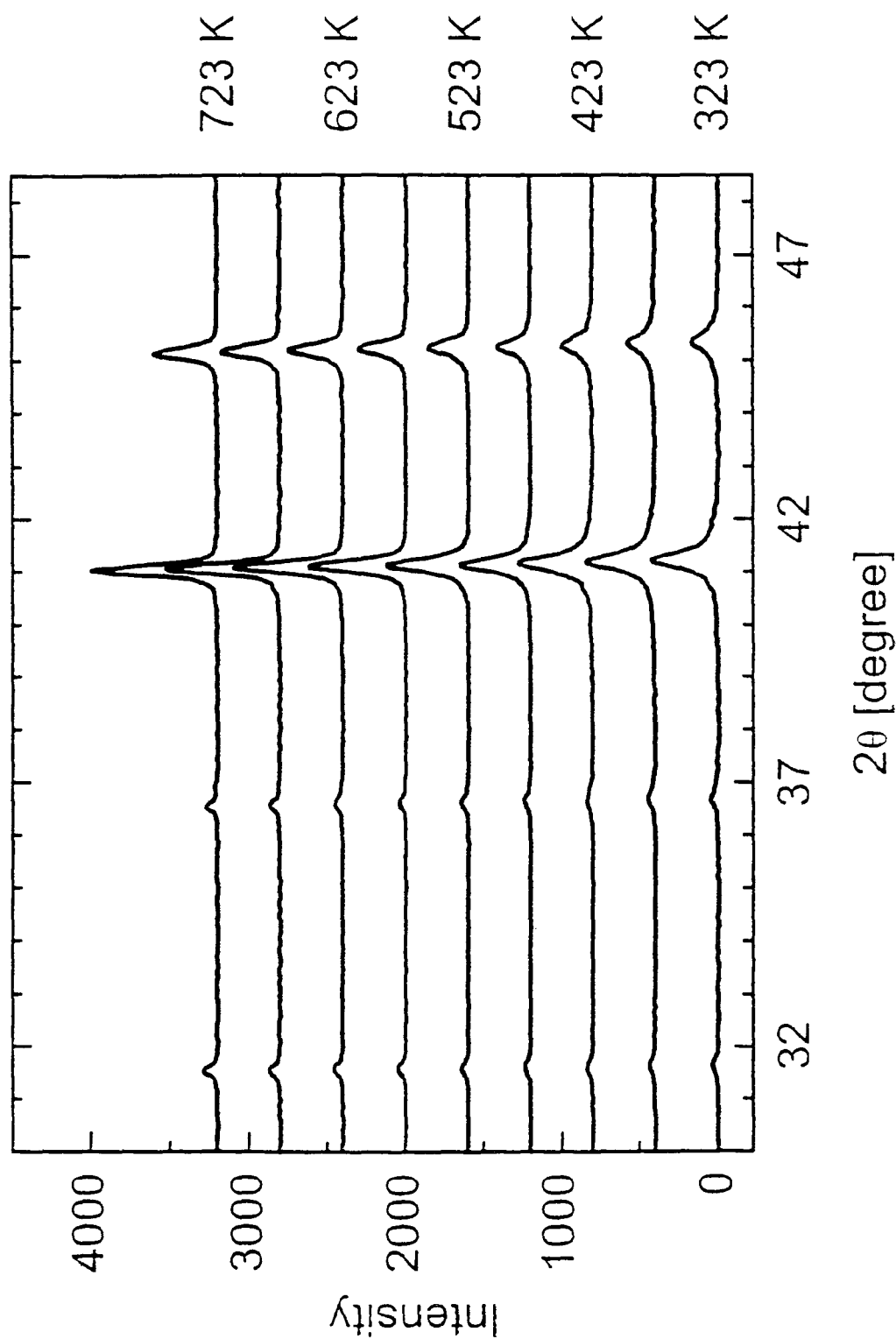
FIG. 2 shows the evolution of in situ XRD patterns measured during thermal treatment of PdGa in 50% hydrogen in helium from 323 to 723 K.

Both, PdGa and $Pd_3Ga_7$ showed a remarkable stability and structural integrity upon the above thermal treatment in various reactive gas atmospheres at temperatures commonly used for selective hydrogenations. This could be demonstrated for example by in situ X-ray diffraction (as described above), as well as by thermal gravimetric analysis (TG and DSC). Representative XRD patterns measured during thermal treatment of PdGa in 50% hydrogen in helium from 323 to 723 K are shown in FIG. 2. As can be seen, no additional diffraction lines corresponding to Pd metal, PdO, or $Ga_2O_3$ were detected. The observed narrowing of the diffraction lines is indicative of crystallite growth of the PdGa material. However, up to 500 K which is the typical temperature employed for selective hydrogenations, the crystallite growth is small.

Catalytic Measurements

Catalytic investigations were performed in a plug flow reactor consisting of a quartz tube with a length of 300 mm, an inside diameter of 7 mm and equipped with a sintered glass frit to support the catalyst bed. For temperature control, a thermocouple was located next to the heating wire wound around the reactor. A second thermocouple was placed inside the reactor to measure the temperature of the catalyst bed. The reactant gases were mixed with Bronkhorst mass flow controllers (total flow 30 ml/min). A Varian CP 4900 Micro gas chromatograph (GC) and a Pfeiffer omnistar quadropol mass spectrometer (MS) were used for effluent gas analysis. The Varian MicroGC contains three modules, each with an individual column and a thermal conductivity detector. Hydrogen and helium of the feed gas, and possible oxygen and nitrogen impurities because of leaks in the set-up were separated on a molsieve column. Acetylene, ethylene, and ethane were separated on an alumina column. The total concentration of $C_4$ hydrocarbons (1-butene, 1,3-butadiene, n-butane, trans and cis-2-butene) was determined using a siloxane (dimethylpolysiloxane) column. Higher hydrocarbons were also separated on the siloxan column but not further quantified because of the presence of many different $C_6$ and $C_8$ hydrocarbons and their low total concentration (less than 0.1% of absolute product stream concentration). Argon (6.0) and helium (6.0) were used as carrier gases for the molsieve column and for the other columns, respectively. A measurement cycle including stabilization, sampling, injection, and separation took between 4 and 5 minutes.

Acetylene hydrogenation experiments were carried out under the condition of 0.5% acetylene, 5% hydrogen, and 50% ethylene in helium. All gases were obtained from Westfalen Gas (Germany).

Activity and selectivity of the materials in the hydrogenation of acetylene were measured by temperature-programmed and by isothermal experiments. The experiments were performed at 473 K in the isothermal mode. The conversion rate was calculated using the following equation:

$$Conv = \frac{(C_{bypass} - C_x)}{C_{bypass}}$$

where $C_X$ is the acetylene concentration in the product stream and $C_{bypass}$ is the acetylene concentration in the feed before the reaction. The selectivity was calculated from the following equation, with $C_{bypass}$ being the acetylene concentration before the reactor and $C_X$ the acetylene concentration after the reactor:

$$Sel = \frac{(C_{bypass} - C_x)}{C_{bypass} - C_x + C_{ethane} + 2xC_{C4Hx}}$$

Calculation of the selectivity assumes that acetylene is only hydrogenated to ethylene, which may be further hydrogenated to ethane. The amount of $C_4$ hydrocarbons and carbon deposits formed was supposed to be negligible. In addition to hydrogenation of acetylene to ethane, ethylene from feed may be hydrogenated to ethane, which is included in the selectivity equation. In order to measure selectivity in acetylene hydrogenation at the same conversion, different amounts of catalysts were used according to their specific activity determined in a previous experiment.

Activity of the samples was calculated using following equation:

$$Act = \frac{ConvC_{feed}C_{exp}}{m_{cat}}$$

where Conv is the calculated acetylene conversion, $C_{feed}$ is the concentration of acetylene in feed, i.e. 0.5%, $m_{cat}$ the amount of used catalyst in g and constant $C_{exp}$ is 1.904 g/h and contains experimental parameters like total gas flow (30 ml), temperature (300 K) and pressure (1013 mbar) and is based on the perfect gas model.

The samples were diluted with 50 mg boron nitride (hexagonal, 99.5%, 325 mesh, Aldrich). A commercial Pd on alumina catalyst (5 wt % Pd, Aldrich) was used as a reference. Additionally, an unsupported palladium silver alloy was used as a benchmark catalyst. The Pd—Ag alloy ($Pd_{20.28}Ag_{79.72}$, referred to as $Pd_{20}Ag_{80}$ in the following) was prepared by melting the corresponding physical mixture of the elements 1.20405 g Ag (99.995% ChemPur) and 0.30348 g Pd (99.95% ChemPur)) three times in an arc melter under argon. Subsequently, the regulus obtained was enclosed in an evacuated quartz glass ampoule and heated at 800° C. for six days. After the heat treatment, the regulus was powdered and phase purity of the Pd—Ag alloy obtained was confirmed by X-ray powder diffraction.

In the case of $Pd_2Ge$, PdZn and PtZn, the intermetallic compound was ground in a mortar and the amount of catalyst was adjusted to reach more than 90% conversion.

Examples 1 and 2, Comparative Examples 1 and 2

The activity, selectivity, and long-term stability of untreated Pd—Ga intermetallic compounds (PdGa, Example 1 and $Pd_3Ga_7$, Example 2) in acetylene hydrogenation were determined in an excess of ethylene (0.5% $C_2H_2$+5%

$H_2+50\%\ C_2H_4$) and compared to the catalytic performance of Pd/Al$_2$O$_3$ (Comparative Example 1) and a Pd$_{20}$Ag$_{80}$ alloy (Comparative Example 2).

Isothermal catalysis experiments were performed by heating the untreated intermetallic compounds and the reference materials (PdGa: 40 mg, Pd$_3$Ga$_7$: 100 mg, Pd/Al$_2$O$_3$: 0.15 mg, and Pd$_{20}$Ag$_{80}$:200 mg) in helium to a reaction temperature of 473 K followed by switching to the ethylene-rich feed.

Figure 3A:
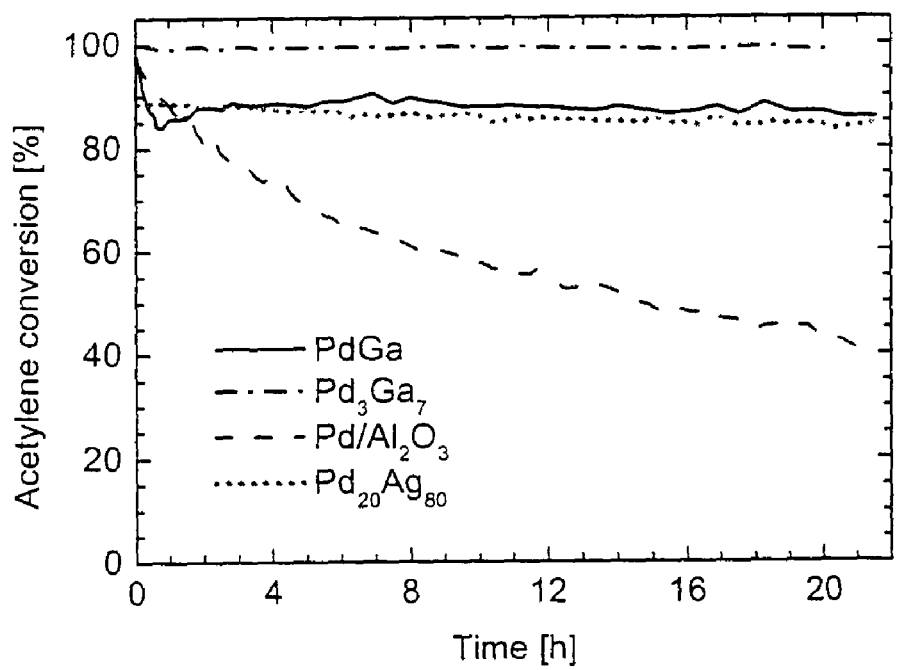
FIG. 3 shows the conversion (FIG. 3a) and selectivity (FIG. 3b) of PdGa (40 mg), $Pd_3Ga_7$ (100 mg), $Pd/Al_2O_3$ (0.15 mg), and $Pd_{20}Ag_{80}$ (200 mg) in the hydrogenation of acetylene in admixture with an excess of ethylene at 473 K.
Figure 3B:
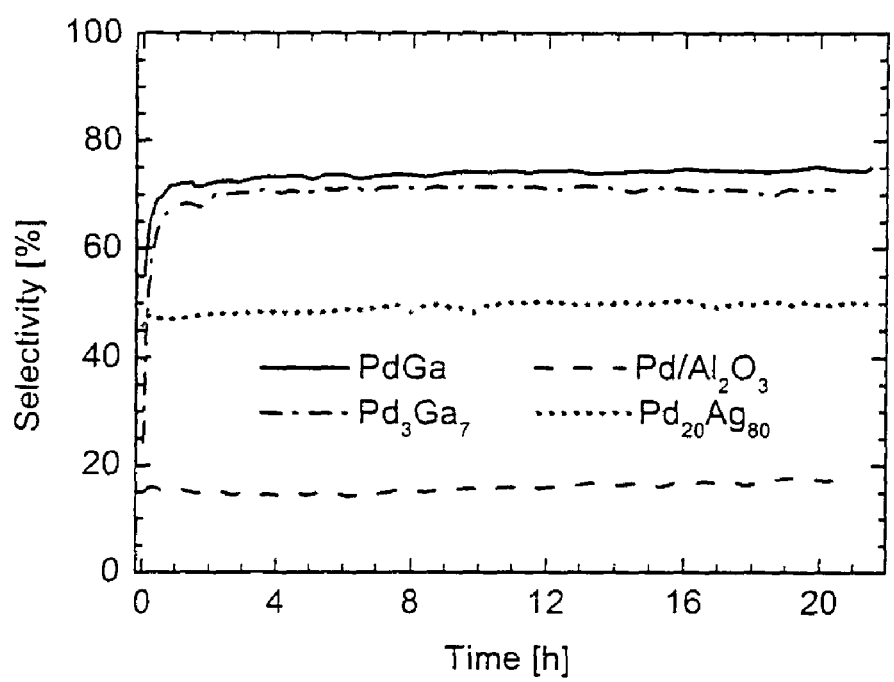

The acetylene conversion and the corresponding selectivity obtained are plotted in FIG. 3a and FIG. 3b. During 20 hours time on stream Pd$_3$Ga$_7$ showed a constant acetylene conversion of 99%. PdGa reached a constant acetylene conversion of about 90% after two hours time on stream. Pd$_{20}$Ag$_{80}$ showed a nearly constant conversion level at 85%, whereas Pd/Al$_2$O$_3$ exhibited a strong deactivation from 100% to 40% conversion during 20 hours time on stream. In addition to a high conversion of acetylene, the untreated intermetallic compounds PdGa and Pd$_3$Ga$_7$ possessed a high long-time stable selectivity of about 70% compared to 50% selectivity of Pd$_{20}$Ag$_{80}$, and only 20% selectivity of Pd/Al$_2$O$_3$ (see also Table 1 the rows with "—" in the column "pH of etching solution").

Examples 3 and 4

Isothermal catalysis experiments were performed by heating the chemically etched (by means of aqueous ammonia solution) intermetallic compounds in helium to a reaction temperature of 473 K followed by switching to the ethylene-rich feed. The results are shown in the following Table 1, which also includes data obtained for the above (Comparative) Examples 1 and 2.

Table 1: Acetylene conversion and selectivity of untreated and chemical etched PdGa, Pd$_3$Ga$_7$, Pd/Al$_2$O$_3$, and Pd$_{20}$Ag$_{80}$ after 20 h in an excess of ethylene at 473 K.

| Sample | pH of etching solution | sample mass [mg] | acetylene conversion % | Selectivity % | Activity [g/g$_{cat}$ · h] |
| --- | --- | --- | --- | --- | --- |
| PdGa | — | 40.0 | 86 | 75 | 0.205 |
| PdGa (Ex. 3) | 9.0 | 5.00 | 93 | 64 | 1.771 |
| Pd$_3$Ga$_7$ | — | 100 | 99 | 71 | 0.094 |
| Pd$_3$Ga$_7$ (Ex. 4) | 10.5 | 7.00 | 98 | 55 | 1.333 |
| Pd/Al$_2$O$_3$ | — | 0.15 | 43 | 17 | 27.29 |
| Pd$_{20}$Ag$_{80}$ | — | 200 | 83 | 49 | 0.040 |

Chemical etching of PdGa at a pH of 9.0 (m=5 mg) resulted in 93% acetylene conversion and 64% selectivity after 20 hours time on stream. This corresponds to an eight times higher activity compared to untreated PdGa (m=40 mg).

Chemically etched Pd$_3$Ga$_7$ also exhibited an increased activity in acetylene hydrogenation. 7 mg of Pd$_3$Ga$_7$ etched at a pH of 10.5 were sufficient to reach a similar acetylene conversion like 100 mg untreated Pd$_3$Ga$_7$.

The above shows that the activity of PdGa and Pd$_3$Ga$_7$ in the selective acetylene hydrogenation can be increased by chemical etching while maintaining a selectivity superior to conventional hydrogenation catalysts.

Examples 5 and 6, Comparative Example 3

The activity, selectivity and long-term stability of Pd$_2$Ga intermetallic compounds in as-prepared form after grinding in a mortar (Example 5) and after milling (Example 6) in acetylene hydrogenation with an excessive amount of ethylene (0.5% $C_2H_2$+5% $H_2$+50% $C_2H_4$) were determined and compared to the catalytic performance of Pd/Al$_2$O$_3$ (Comparative Example 3).

Isothermal catalysis experiments were performed by heating the intermetallic Pd$_2$Ga compounds and the reference materials (Pd$_2$Ga as prepared: 10 mg; Pd$_2$Ga milled using a swing mill: 0.8 mg; Pd/Al$_2$O$_3$: 0.1 mg) in helium to a reaction temperature of 473 K, followed by switching to the ethylene-rich feed.

Figure 4A:
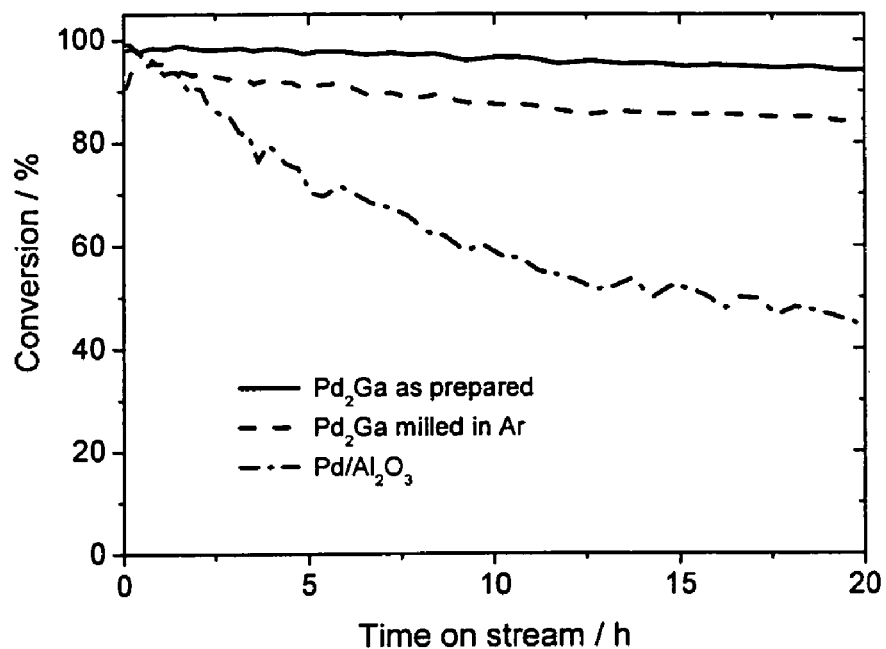
FIG. 4 shows the conversion (FIG. 4a) and selectivity (FIG. 4b) of as-prepared $Pd_2Ga$ (10 mg), $Pd_2Ga$ milled in argon (0.8 mg) and $Pd/Al_2O_3$ (0.1 mg) in the hydrogenation of acetylene in admixture with an excess of ethylene at 473 K.
Figure 4B:
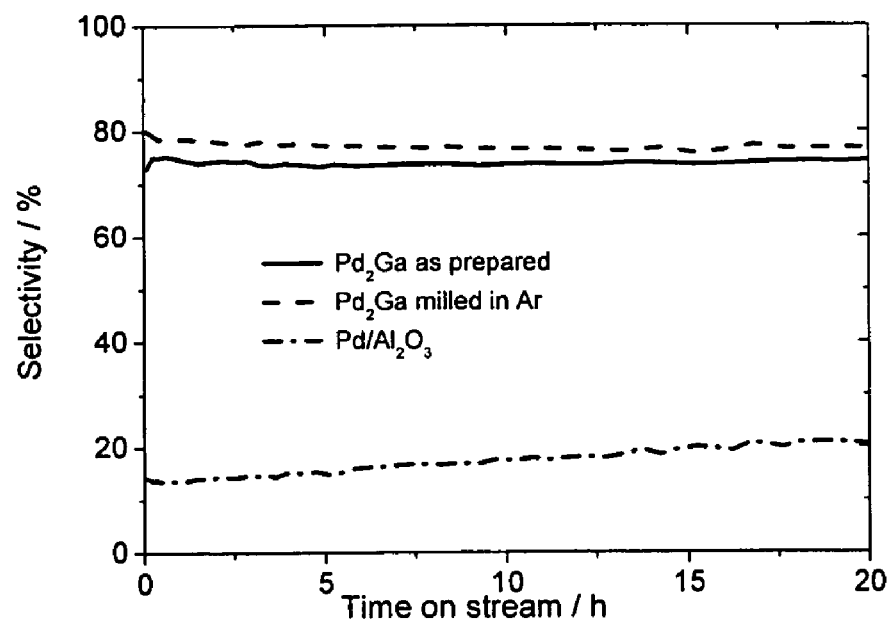

FIGS. 4a and 4b show the acetylene conversion and the corresponding selectivity obtained in the above experiments. As can be seen, Pd$_2$Ga shows excellent activity, stability and selectivity.

The catalytic results after 20 h time on stream are compiled in the following table. As can be seen, the activity of Pd$_2$Ga can be increased significantly by milling (note that only 0.8 mg milled Pd$_2$Ga was used in Example 6) so as to increase the specific surface area, while retaining the high selectivity.

Table 2: Acetylene conversion, selectivity and activity of as-prepared and milled Pd$_2$Ga and Pd/Al$_2$O$_3$ after 20 h in an excess of ethylene at 473 K.

| Sample | Sample treatment | Sample mass [mg] | Acetylene conversion [%] | Selectivity [%] | Activity [g/g$_{cat}$ · h] |
| --- | --- | --- | --- | --- | --- |
| Pd$_2$Ga (Ex. 5) | None | 10 | 94 | 74 | 0.89 |
| Pd$_2$Ga (Ex. 6) | Milled in argon | 0.8 | 84 | 77 | 10.0 |
| Pd/Al$_2$O$_3$ (Comp. Ex. 3) | None | 0.1 | 44 | 20 | 41.89 |

Examples 7 and 8

Figure 5A:
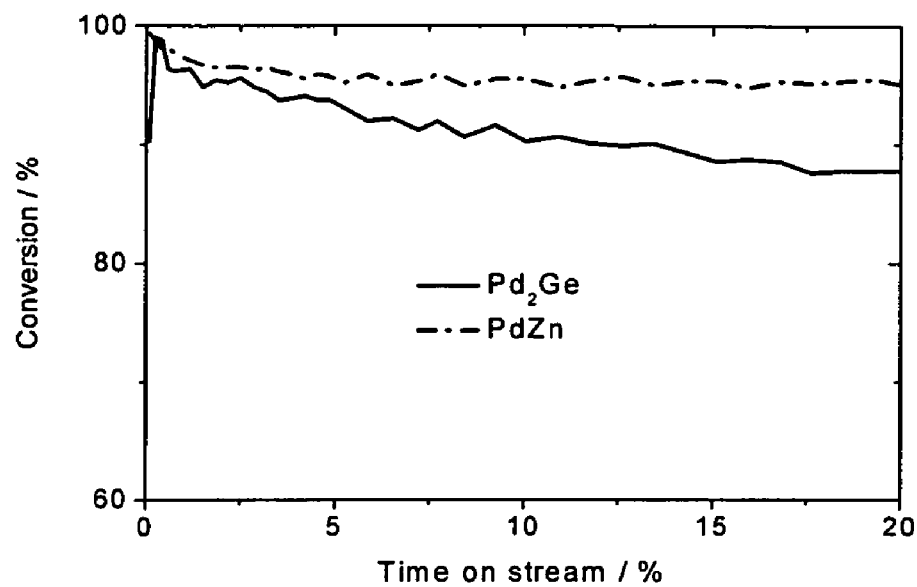
FIG. 5 shows the conversion (FIG. 5a) and selectivity (FIG. 5b) of $Pd_2Ge$ (0.5 mg) and PdZn (100 mg) in the hydrogenation of acetylene in admixture with an excess of ethylene at 473 K.
Figure 5B:
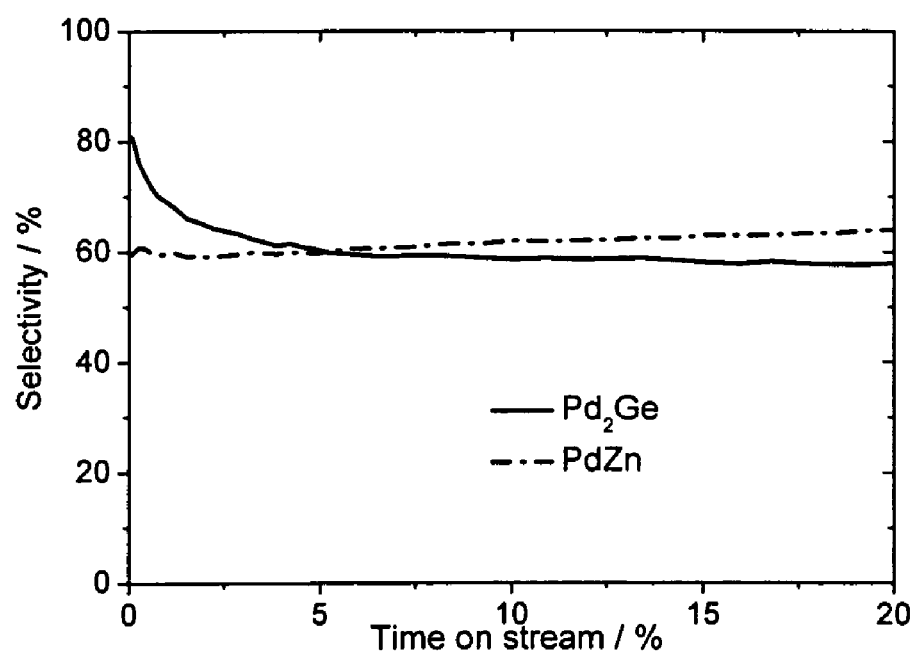

Catalytic experiments were carried out using Pd$_2$Ge (0.5 mg) and PdZn (100 mg) as ordered intermetallic compounds in the hydrogenation of acetylene in the presence of excessive ethylene at 473 K. Isothermal catalysis experiments were performed similar to Examples 1 and 2. The results are shown in FIGS. 5a and 5b.

As can be seen, Pd$_2$Ge which is used in Example 7 in an amount of only 0.5 mg is highly active. Moreover, Pd$_2$Ge and PdZn exhibit a high selectivity in the conversion of acetylene to ethylene in the presence of a large excess of ethylene.

Example 9

Figure 6:
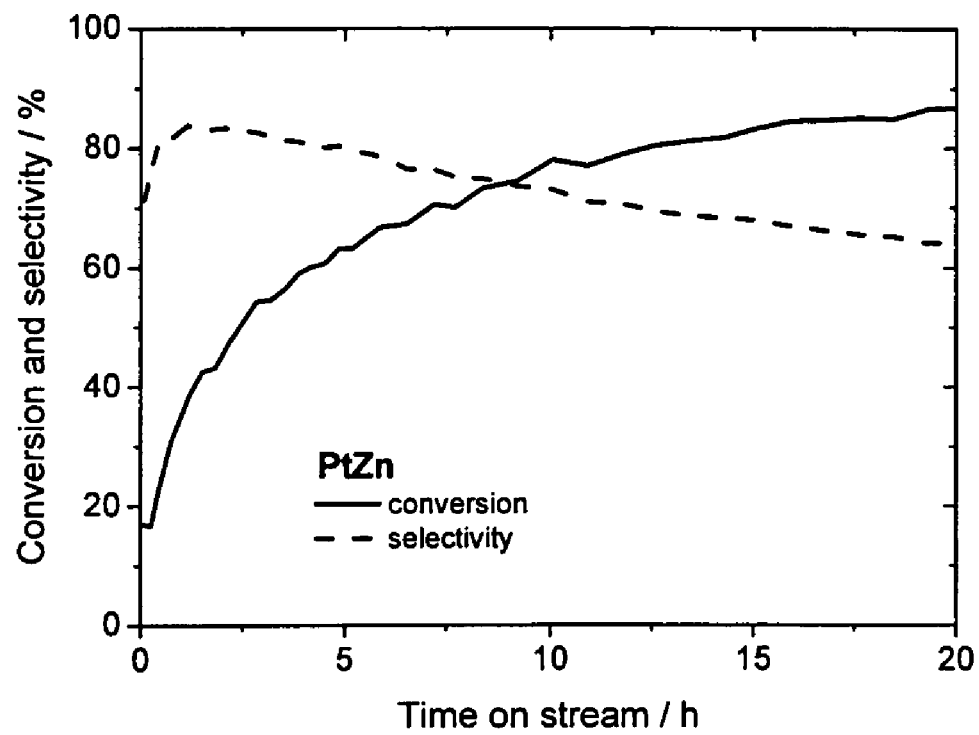
FIG. 6 shows the conversion and selectivity of the hydrogenation of acetylene to give ethylene in the presence of an excess of ethylene at 473 K using PtZn as a catalyst.

Acetylene was hydrogenated in the presence of an excess of ethylene at 473 K using 100 mg PtZn ordered intermetallic compound as a catalyst. Isothermal catalysis experiments were performed similar to Examples 1 and 2. As shown in FIG. 6, a high selectivity to the desired ethylene at a high conversion is achieved.

What is claimed is:

1. A process for the hydrogenation of at least one unsaturated hydrocarbon compound, the process comprising reacting the unsaturated hydrocarbon compound with hydrogen in the presence of a hydrogenation catalyst,
    wherein the hydrogenation catalyst comprises an ordered intermetallic compound,
    wherein the intermetallic compound comprises at least one kind of metal of type A capable of activating hydrogen, and at least one kind of metal of type B not capable of activating hydrogen, and the structure of the intermetallic compound is such that at least one kind of type A metals is mainly surrounded by atoms of type B metals, wherein the unsaturated hydrocarbon compound is selected from the group consisting of alkynes, dialkynes, trialkynes and polyalkynes, and wherein the hydrogenation catalyst comprises PdGa, $Pd_2Ga$, or $Pd_3Ga_7$.

2. The process according to claim 1, wherein the hydrogenation is a selective hydrogenation.

3. The process according to claim 1 or 2, wherein the unsaturated hydrocarbon is ethyne which is converted to ethene through the selective hydrogenation.

4. The process according to claim 3, wherein the ethyne is present in admixture with an excess of ethene.

5. The process according to claim 1, wherein the intermetallic compound is subjected to surface etching prior to use as a hydrogenation catalyst in the selective hydrogenation.

6. The process according to claim 5, wherein the etching is carried out using an alkaline etching solution.

7. The process according to claim 6, wherein the intermetallic compound is PdGa or $Pd_3Ga_7$ and the pH of the alkaline etching solution is in the range of 8.0 to 10.5.

8. The process according to claim 1, wherein the intermetallic compound is comminuted prior to use as a hydrogenation catalyst in the selective hydrogenation.

9. A process of hydrogenation comprising reacting an unsaturated hydrocarbon compound with hydrogen in the presence of a binary Pd-Ga ordered intermetallic compound as a catalyst.

10. The process according to claim 9, wherein the molar ratio of Pd and Ga in the ordered intermetallic compound is 20:1 to 1:20.

11. The process according to claim 10, wherein the ordered intermetallic compound is PdGa, $Pd_2Ga$ or $Pd_3Ga_7$.

12. A catalyst comprising a support and an ordered intermetallic compound supported thereon, wherein the intermetallic compound is a binary Pd-Ga ordered intermetallic compound selected from PdGa, $Pd_2Ga$, and $Pd_3Ga_7$.

* * * * *